United States Patent [19]

Lindsey, Jr. et al.

[11] 4,298,531
[45] Nov. 3, 1981

[54] OXIDATION OF BUTADIENE TO FURAN

[75] Inventors: Richard V. Lindsey, Jr.; William W. Prichard, both of Hockessin, Del.

[73] Assignee: E. I. Du Pont de Nemours and Company, Wilmington, Del.

[21] Appl. No.: 215,711

[22] Filed: Dec. 15, 1980

Related U.S. Application Data

[63] Continuation-in-part of Ser. No. 108,820, Dec. 31, 1979, abandoned.

[51] Int. Cl.$^3$ .......................................... C07D 307/36
[52] U.S. Cl. .............................................. 260/346.11
[58] Field of Search .................................... 260/346.11

[56] References Cited

U.S. PATENT DOCUMENTS 3,238,225  3/1966  Brill et al. ...................... 260/346.11
4,172,838  10/1979  Garnett et al. .................. 260/346.11

FOREIGN PATENT DOCUMENTS 52-77049  6/1977  Japan .
1025679  4/1966  United Kingdom .
1508331  4/1978  United Kingdom .
265119   6/1970  U.S.S.R. .

OTHER PUBLICATIONS

Smith et al., Inorg. Chem., vol. 12 (1973) pp. 331–338.

*Primary Examiner*—Richard Raymond

[57] ABSTRACT

Process for preparing furan from 1,3-butadiene, the process comprising contacting the butadiene, at about 65° C. to about 120° C., with a solution having a pH of 0–2.5 and containing palladium ions and a heteropolyacid having a redox potential greater than 0.5 volt, to produce furan.

15 Claims, No Drawings

OXIDATION OF BUTADIENE TO FURAN

CROSS-REFERENCE TO RELATED APPLICATION

This is a continuation-in-part of application Ser. No. 108,820 filed Dec. 31, 1979, now abandoned.

DESCRIPTION

Technical Field

This invention relates to a catalytic process for the preparation of furan from 1,3-butadiene.

Background

Furan, a well-known industrial chemical, can be synthesized in a variety of ways. A common synthetic organic route involves the decarboxylation of 2-furoic acid, the latter being preparable from furfural. Another method that can be used to produce furan involves the ethynylation reaction between acetylene and formaldehyde, via the intermediate 2-butyne-1,4-diol. Furan is also obtainable by the catalytic oxidation of 1,3-butadiene. Such a process, employing as the catalyst a palladium salt and a thallium or indium compound, is disclosed in Japanese Patent Application Publication No. 52-77049. U.S.S.R. Pat. No. 265,119 discloses a catalytic process for the conversion of 1,3-butadiene to furan, the process being carried out in the presence of a catalytic mixture of an aqueous solution of a divalent copper salt and palladium chloride at a pH of 0.1–0.5 and a temperature of 60°–110° C. U.S. Pat. No. 4,172,838 discloses a catalytic process for oxidizing 1,3-butadiene to furan, the catalyst consisting of an aqueous solution of cupric and cuprous salts, iodide ion and hydrochloric acid.

Disclosure of Invention

For further comprehension of the invention, and of the objects and advantages thereof, reference may be made to the following description and to the appended claims in which the various novel features of the invention are more particularly set forth.

The invention herein resides in a process which can be carried out economically at a low temperature in low cost equipment. More specifically, the invention resides in a process for converting 1,3,-butadiene to furan. Still more specifically, in the process of the invention, 1,3-butadiene is contacted, at about 65° C. to about 120° C., with a solution having a pH of 0–2.5 and containing palladium ions and a heteropolyacid having a redox potential greater than 0.5 volt, to produce furan which can be removed from the system and recovered.

The palladium ions of the solution can be provided by palladium or any palladium salt or oxide which dissolves or reacts in the solution and forms palladium ions. Examples of such materials include $PdCl_2$, $Pd(NO_3)_2$, $Pd(OCOCH_3)_2$, $K_2PdCl_4$ and $PdO$. Other sources of the palladium ion include $[(C_6H_5)_3P]_2PdCl_2$, $[(C_6H_5)_3As]_2PdCl_2$, $(C_6H_5NH_2)_2PdCl_2$, $(pyridyl)_2PdCl_2$, $[(C_2H_5)_3P]_2PdCl_2$, $[(C_2H_5)_4N]_2PdCl_4$, palladium salicylate and palladium on an inert support.

The heteropolyacid, which is believed to oxidize any free palladium formed in the reaction back to ionic palladium, can be any such acid with a redox potential greater than 0.5 volt. A heteropolyacid is an organic acid having an anion which contains oxygen and more than one other element other than hydrogen. Examples thereof include $AsMo_9O_{34}^{-9}$, $PW_{12}O_{40}^{-3}$ and $PMo_6V_6O_{40}^{-9}$. The polyacid can be prepared as a salt, such as the sodium, potassium or ammonium salt, and converted to the acid form either by means of an acid, for example, sulfuric acid or phosphoric acid, or by means of an ion exchange resin. Examples of specific heteropolyacids and salts thereof which are useful herein include $Na_4SiW_{12}O_{40}$, $K_4SiW_{12}O_{40}$, $H_4PW_{12}O_{40}$, $K_5H_2PW_8V_4O_{40}$, phosphomolybdic acid, $H_3PW_{12}O_{40}$, $H_9PMo_6V_6O_{40}$, $H_{11}PMo_4V_8O_{40}$, $H_6PMo_9V_3O_{40}$ and $H_4PMo_{11}VO_{40}$. The preferred heteropolyacids are the phosphomolybdovanadic acids and the phosphotungstovanadic acids, of which the last four compounds recited immediately above are representative.

Any suitable acid, for example, hydrochloric acid, can be used to maintain the pH of the catalyst solution at the requisite 0–2.5. Preferred acids include sulfuric acid and phosphoric acid.

The process of the invention can be carried out at about 65° to about 120° C., preferably about 75° C. to about 105° C. At temperatures below about 75° C. the reaction rates are generally lower. Moreover, if the reaction temperature is above about 105° C., the furan which is produced should be removed from the system promptly to minimize degradation. Although the process is conveniently carried out at atmospheric pressure, it is to be understood that it can be carried out at other pressures if more convenient, for example, at superatmospheric pressure.

As indicated above, palladium ions must be present during the carrying out of the process. As furan is produced, the ionic palladium is reduced and thus requires oxidation (activation). Reactivation can be effected by contacting the used ("spent") solution with air or oxygen. Alternatively, to avoid a separate regeneration step, air or oxygen can be introduced along with the 1,3-butadiene as the process of the invention is being carried out so as to maintain the palladium substantially in its oxidized valence state.

When the process of the invention is carried out using the separately regenerative mode of oxidizing the palladium, the concentration of 1,3-butadiene in the feed stream can be very high. If desired pure butadiene can be contacted with the palladium ion/heteropolyacid catalyst solution and any unreacted butadiene can be used to sweep the furan from the system. When it becomes desirable to regenerate the catalyst solution, introduction of fresh butadiene is interrupted and air or oxygen is introduced. When the continuously regenerative mode of oxidizing the palladium is used, it is preferable to introduce an inert diluent, such as nitrogen, into the system along with the butadiene and air or oxygen, if necessary, in order to avoid the formation of explosive mixtures of materials.

Regeneration of the catalyst solution takes place more rapidly at the higher operating temperatures. At temperatures below about 75° C. the regeneration proceeds too slowly to sustain continuous operation. Therefore, when the continuously regenerative mode of oxidizing is used, the invention process temperature should be about 75° C. to about 120° C., preferably about 75° C. to about 105° C. When the separate regenerative mode of oxidizing is used, the temperature during the regeneration step should be about 75° C. to about 120° C. However, if the invention process is carried out at about 75° C. to about 105° C., the separate regenerative mode can also be carried out at this temperature.

The following examples demonstrate the use of various heteropolyacids, all of which have been employed in their hydrated form, in the process of the invention. The heteropolyacids which are exemplified include $H_9PMo_6V_6O_{40}$ (Examples 1, 4 and 5), $H_{11}PMo_4V_8O_{40}$ (Example 2) and $H_6PMo_9V_3O_{40}$ (Example 6). These compounds can be represented by the general formula $H_{3+n}PM_{12-n}V_nO_{40}\cdot xH_2O$ wherein M is Mo or W, n is 1–10 and x is the number of moles of water of hydration per mole of heteropolyacid and is greater than 0 but less than 32. Unless specified otherwise all parts and percentages recited in the examples are by weight.

EXAMPLE 1

A solution of $H_9PMo_6V_6O_{40}$ was prepared according to the procedure of British Pat. No. 1,508,331, Example 6. A 75 mL aliquot of this solution containing 0.157 mole of the heteropolyacid, which had a redox potential of $+0.77$ V, was combined with 0.1 g of $PdCl_2$ heated at 85° C. in a flask fitted with an efficient mechanical stirrer; the pH of the solution was adjusted to 0.8 with $H_3PO_4$. A gas stream containing 61% 1,3-butadiene and 39% dichlorodifluoromethane (Freon® F-12 as an inert diluent and an internal standard to permit calculation of butadiene conversion by gas chromatographic analysis) was pumped through the solution at 15 mL/min at atmospheric pressure. After 10 min passage of this feed, oxygen was pumped through the solution for 10 min and the collected gases were analyzed on a $10' \times \frac{1}{8}''$ (3.048 m $\times$ 3.175 mm) Poropak® QS gas chromatographic column at 150° C. and 50 mL/min He flow. By comparison of the relative areas of the butadiene peak with that of the Freon® F-12 peak in the inlet gas and in the exit gas, the conversion of butadiene was found to vary from 4.35% to 9% with a furan yield, based on butadiene converted, of 28.8% to 79%. During three oxidation-regeneration cycles, each of 20 min duration, the average conversion was 4.7% and the average furan yield was 55.7%. The pH at the end of the experiment was 1.25.

EXAMPLE 2

A solution of $H_{11}PMo_4V_8O_{40}$, which has a redox potential of $+0.8$ V, was prepared by adding sufficient conc. $NH_4OH$ to a mixture of 19.69 g (0.01 mole) of $H_3PMo_{10}O_{34}\cdot 12H_2O$, 24.57 g (35% excess) of $V_2O_5$, 1.04 g of $H_3PO_4$ and 150 mL of $H_2O$ to obtain a red-brown solution. On standing, 13.25 g of a crystalline ammonium salt precipitated. This was dissolved in water, deionized by passage through a column containing 150 mL of Rexyn® 101 $H^+$ ion exchange resin having a total capacity of 285 mole equivalents of $H^+$. The effluent was concentrated to 25 mL, giving a solution with a pH of 0.8. Charged into a small reaction vessel were 3 mL of this solution and 0.1 g of $K_2PdCl_4$; after being heated to 79° C. a feed gas containing 34.5% air, 49.6% 1,3-butadiene and 15.3% Freon® F-12 was bubbled through the solution at 19 mL/min. The % butadiene conversion dropped from 28.1% to 4.1% over one hour while the furan yield rose from an initial 21.4% to 55–57%.

EXAMPLE 3

A solution was prepared so as to contain 25.0 g of $K_5H_2PW_8V_4O_{40}$ (prepared as described by D. P. Smith and M. T. Pope, Inorg. Chem. 12, 331 (1973)), 2.5 g of $K_2PdCl_4$ and 10 mL of conc. HCl in 40 mL of $H_2O$. The clear red solution was placed in a round bottom flask and stirred; a mixture of 1,3-butadiene and air was bubbled through the solution at 90° C. Assay of the off-gas on a Poropak® N column at 175° C. with a helium flow of 15 mL/min showed the presence of furan in low conversion. The reaction was continued for 16 h, at the end of which time the solution had become greenish black and furan production had ceased.

EXAMPLE 4

A glass U-tube was packed with 3.0 g of a commercial 10 wt % palladium-on-carbon hydrogenation catalyst (Engelhardt) and plugged at each end with glass wool. The glass wool and catalyst were saturated with a solution of 3.0 g of $H_9PMo_6V_6O_{40}$, prepared as in Example 1, in 7.5 ml of water. Oxygen was bubbled through the U-tube at a rate of 14 ml/min for about 5 min while the tube was heated to 90° C. in an oil bath. Then, a mixture of 1,3-butadiene and Freon® F-12 (mole ratio 3.61) was passed through the U-tube for 10 min at a rate of 14 ml/min and the product was collected in an impermeable plastic bag. Analysis of the contents of the bag showed a conversion of butadiene of 12.8% and a furan yield of 1.1%. Butadiene/Freon® F-12 feed was then resumed for 10 min, followed by oxygen for 10 min. The product again was collected in a plastic bag. Analysis of the material collected showed a butadiene conversion of 5.8% and a furan yield of 6.25%. Repitition of the preceding feed/oxygen sequence resulted in a butadiene conversion of 8.8% and a furan yield of 6.4%.

EXAMPLE 5

A 250 mL flask fitted with a mechanical stirrer was placed in a bath heated at 86° C. and a gas stream containing 55% air (diluted to 10% oxygen with nitrogen), 12% Freon® F-12 and 33% 1,3-butadiene was passed through the flask. A solution of 14.35 g of $H_9PMo_6V_6O_{40}$ and 0.1 g of $K_2PdCl_4$ in 25 mL of water was added. The feed gas was recycled through this solution at about 25 mL/min. After 30 min. recycle the conversion of butadiene was 47.2% and the furan yield was 22.3%. No by-product peaks were identified by gas chromatography on a Poropak® QS column run at 175° C. with a 50 mL/min helium flow. After 60 min butadiene conversion was 57.2% and furan yield was 27.1%. The gas was swept from the system by a stream of air for 30 min. and a new feed gas containing 44% air, 16.8% Freon® F-12 and 38.7% 1,3-butadiene was recycled through the solution as previously described. After 60 min the conversion of butadiene was 8.7% and the yield of furan was 38.8%. A trace of acetaldehyde was also present in the gas stream.

EXAMPLE 6

A small U-tube packed with glass helices was charged with a solution containing 5 g of $H_6PMo_9V_3O_{40}$ in 5 mL of $H_2O$ and 10 mL of 25% $H_2SO_4$. One hundred milligrams of $K_2PdCl_4$ was added. The pH of the final solution was 0.6. A gas stream containing 22% air, 19% nitrogen, 36.3% 1,3-butadiene and 22.5% Freon® F-12 was passed through the solution at 13.6 mL/min and 68° C. for 40 min. The exit gas was collected in a large plastic bag and assayed by gas chromatography. The conversion of butadiene was 11.9% and the yield of furan was 16.5%. Acetaldehyde was also present in the amount of 3.5%.

BEST MODE FOR CARRYING OUT THE INVENTION

In a preferred mode of operation, a mixture of 1,3-butadiene and air or oxygen with added inert gas such as nitrogen to avoid explosive mixtures is contacted at about 75° C. to about 105° C., with a solution having a pH of 0–2.5 and containing palladium ions and a heteropolyacid having a redox potential of greater than 0.5 volt to produce furan which is removed and recovered.

INDUSTRIAL APPLICABILITY

The process of the invention provides a ready source of furan which, if desired, can be converted to tetrahydrofuran and/or 1,4-butanediol by well known procedures.

Although preferred embodiments of the invention have been illustrated and described, it is to be understood that there is no intent to limit the invention to the precise constructions herein disclosed and the right is reserved to all changes and modifications coming within the scope of the invention described above and set forth in the appended claims.

We claim:

1. Process for preparing furan from 1,3-butadiene, the process comprising contacting the butadiene, at about 65° C. to about 120° C., with a catalyst solution having a pH of 0–2.5 and containing palladium ions and a heteropolyacid having a redox potential greater than 0.5 volt and being of the formula $H_{3+n}PM_{12-n}V_nO_{40}\cdot xH_2O$ wherein M is Mo or W, n is 1–10 and $0<x<32$, to produce furan.

2. Process of claim 1 wherein the temperature is about 75° C. to about 105° C.

3. Process of claim 1 wherein the catalyst solution which has contacted the butadiene and has been converted to a reduced form is regenerated by oxidation.

4. Process of claim 3 wherein air or oxygen is used to effect regeneration of the catalyst solution.

5. Process of claim 4 wherein the regeneration is carried out continuously by admixing air or oxygen with the butadiene and the temperature is about 75° C. to about 120° C.

6. Process of claim 5 wherein the temperature is about 75° C. to about 105° C.

7. Process of claim 5 wherein the air or oxygen is diluted with an inert diluent.

8. Process of claim 7 wherein the diluent is nitrogen.

9. Process of claim 4 wherein the regeneration is carried out at about 75° C. to about 120° C. without the addition of fresh butadiene.

10. Process of claim 9 wherein the butadiene and the catalyst solution are contacted at about 75° C. to about 105° C. and wherein the regeneration is carried out at about 75° C. to about 105° C.

11. Process of claim 1 wherein the heteropolyacid is $H_9PMo_6V_6O_{40}$.

12. Process of claim 1 wherein the heteropolyacid is $H_{11}PMo_4V_8O_{40}$.

13. Process of claim 1 wherein the heteropolyacid is $H_6PMo_9V_3O_{40}$.

14. Process of claim 1 wherein the palladium ions are provided by $PdCl_2$.

15. Process of claim 1 wherein the palladium ions are provided by $K_2PdCl_4$.

* * * * *